United States Patent [19]
Weng et al.

[11] Patent Number: 5,716,778
[45] Date of Patent: *Feb. 10, 1998

[54] CONCENTRATING IMMUNOCHEMICAL TEST DEVICE AND METHOD

[75] Inventors: Litai Weng, Mountain View; David Calderhead, Menlo Park; Pyare Khanna, San Jose; Edwin F. Ullman, Atherton, all of Calif.

[73] Assignee: Abbott Laboratories, Abbott Park, Ill.

[ * ] Notice: The term of this patent shall not extend beyond the expiration date of Pat. No. 4,740,468.

[21] Appl. No.: 351,976

[22] Filed: May 15, 1989

Related U.S. Application Data

[63] Continuation of Ser. No. 164,308, Mar. 4, 1988, Pat. No. 4,879,215, which is a continuation of Ser. No. 701,464, Feb. 14, 1985, Pat. No. 4,740,468.

[51] Int. Cl.$^6$ ..................................... C12Q 1/00
[52] U.S. Cl. ..................... 435/4; 435/5; 435/7.1; 435/7.9; 435/7.92; 435/7.93; 435/975; 436/65; 436/814; 422/55; 422/56; 422/61
[58] Field of Search ................... 422/55, 56, 61; 436/536, 65, 814; 435/4, 5, 7.1, 7.9, 7.92, 7.93, 7.94, 7.95, 805, 806, 970, 971, 975

[56] References Cited

U.S. PATENT DOCUMENTS

| | | |
|---|---|---|
| 4,094,647 | 6/1978 | Deutsch et al. . |
| 4,666,863 | 5/1987 | Edwards et al. ............ 436/514 |
| 4,740,468 | 4/1988 | Weng et al. ................. 435/7 |
| 4,782,016 | 11/1988 | Norton . |
| 4,806,311 | 2/1989 | Greenquist . |
| 4,865,997 | 9/1989 | Stoker . |
| 4,868,108 | 9/1989 | Bahar et al. . |

FOREIGN PATENT DOCUMENTS

| | | |
|---|---|---|
| 189 925 | 8/1986 | European Pat. Off. . |
| 0200381 | 11/1986 | European Pat. Off. . |
| 0217403 | 4/1987 | European Pat. Off. . |
| WO 84/02193 | 6/1984 | WIPO . |
| WO 85/05451 | 12/1985 | WIPO . |

*Primary Examiner*—Laurie A. Scheiner
*Attorney, Agent, or Firm*—David L. Weinstein; Gregory W. Steele

[57] ABSTRACT

A method and device for determining the presence of an analyte in a sample suspected of containing the analyte is disclosed. The method involves contacting a test solution containing the sample and a first member of a specific binding pair with an end portion of a strip of bibulous material capable of being traversed by the test solution through capillary action. The first member of a specific binding pair is capable of binding the analyte. The strip contains a second member of a specific binding pair integral therewith for concentrating and non-diffusively binding the first sbp member at a small situs on the strip separated from the end portion of the strip. The detectible signal is produced in relation to the presence of the analyte in the test solution. The test solution passes through the situs as the test solution traverses the bibulous material. After the test solution has been allowed to traverse at least a portion of the strip, the strip is contacted with a developer solution containing members of a signal producing system in a manner that provides contact of the developer solution with the small situs following its contact with the test solution. The strip is then contacted with any remaining members of the signal producing system. The detectible signal produced at the situs is then compared with the signal detectible at a portion of the strip other than the situs to determine the analyte in the sample. In one embodiment of the invention the signal produced at the small situs has a sharp-edged distinctive pattern that provides a sharp contrast to the signal produced at adjacent sites on the strip when analyte is present in the test solution.

129 Claims, No Drawings

CONCENTRATING IMMUNOCHEMICAL TEST DEVICE AND METHOD

This application is a continuation of Ser. No. 07/164308, filed Mar. 4, 1988 now U.S. Pat. No. 4,879,215, which is a continuation of Ser. No. 06/701464, filed Feb. 14, 1985, now U.S. Pat. No. 4,740,468.

BACKGROUND OF THE INVENTION

1. Field of the Invention

The ability to employ naturally occurring receptors or antibodies directed to specific compounds in assaying for the presence of a compound of interest has created a burgeoning immunoassay business. In each of the assays, a homologous pair of specific binding pair ("sbp") members, usually an immunological pair, involving a ligand and a receptor (antiligand) is involved, wherein one of the sbp members is labeled with a label which provides a detectible signal. The immunoassay methodology results in a distribution of the signal label between signal label bound in a complex of the sbp members and unbound signal label. The differentiation between bound and unbound signal label can be as a result of physical separation of bound from unbound signal label or modulation of the detectible signal between bound and unbound signal label.

For the most part, immunoassays have been directed to quantitative determination of a wide variety of compounds of interest in clinical laboratories requiring relatively sophisticated equipment and careful technique. Immunoassays have found less extensive commercial application where semi-quantitative or qualitative results would be acceptable and the determination would involve non-laboratory personnel, such as in a home or a medical practitioner's office. Even in the clinical laboratory, simple and rapid screening tests employing inexperienced personnel could serve to provide substantial economies.

In developing an immunoassay, there are many considerations. One consideration is to provide substantial differentiation between the observed signal resulting from signal label when bound as compared to unbound. Another consideration is to minimize interference from endogenous materials in the sample suspected of containing the compound of interest. A further consideration is the ease with which the observed signal can be detected and serve to differentiate between concentrations in the concentration range of interest. Other factors include the ease of preparation of the reagents, the accuracy with which samples and reagent solutions must be prepared and measured, the storage stability of the reagents, the number of steps required in the protocol, and the proficiency and accuracy with which each of the steps must be performed. Therefore, in developing an assay which can have application with untrained personnel, such as assays to be performed in the home, in forensic medicine, by medical practitioners, or the like, the observed result should be minimally affected by variations in the manner in which the protocol is carried out or provide for simple techniques for performing the various steps.

2. Description of the Prior Art

A test device for determining a characteristic of a sample, particularly for determining substances in fluid samples, is disclosed in U.S. Pat. No. 4,094,647. A thin layer chromatography device and method of making a chromatography test is disclosed in U.S. Pat. No. 4,384,958. An immunoassay wherein labeled antibody is displaced from immobilized analyte analog is described in U.S. Pat. No. 4,434,236. A device and method for detecting myoglobin is disclosed in U.S. Pat. No. 4,189,304. Test strips for analyzing substances dissolved in liquids are described in U.S. Pat. No. 4,438,067. A multi-layered test device for determining the presence of a liquid sample component and the method of using such a device, are described in U.S. Patent No. 4,160,008. A method for measuring antigen by labeled antigen using insoluble antibody is disclosed in Japanese Patent Application Laid-Open No. 5925/73—Jan. 25, 1973.

A concentrating zone method in heterogeneous immunoassays is disclosed in U.S. Pat. No. 4,366,241. U.S. Pat. No. 4,168,146 describes an immunoassay test strip. U.S. Pat. Nos. 3,990,850 and 4,055,394 describe diagnostic test cards. An automated method for quantitative analysis of biological fluids is described in U.S. Pat. No. 4,327,073. A chromogenic support immunoassay is disclosed in International Application No. PCT/US83/01887.

A wide variety of patents and patent applications provide an extensive literature of different techniques for producing detectible signals in immunoassays. The following list is merely illustrative of some of these techniques which can find application in this invention. The following is a list of United States patents and patent applications and a general statement of the type of label involved:

U.S. Pat. Nos. 3,646,346, Radioactive Label; 3,654,090, 3,791,932 and 3,817,838, Enzyme Labels; 3,996,345, Fluorescer-Quencher Labels; 4,062,733, Radioactive Label; 4,067,959, Fluorescer or Enzyme Label; 4,104,029, Chemiluminescent Label; and 4,160,645, Non-Enzymatic Catalyst Label. See U.S. Pat. Nos. 3,966,879 for an electrophoretic technique employing an antibody zone and 4,120,945 for an RIA where labeled analyte is initially bound to a solid support through antibody. U.S. Pat. No. 4,233,402 employs enzyme pair labels; U.S. Pat. No. 4,720,450, chemically induced fluorescent labels; and U.S. Pat. No. 4,287,300, enzyme anionic charge labels.

SUMMARY OF THE INVENTION

The methods and devices of the present invention are useful for determining the presence of an analyte in a sample suspected of containing the analyte. The device is a strip of bibulous material capable of being traversed by a test solution through capillary migration. The test solution is comprised of the sample and a first member of a specific pair ("sbp member") capable of binding the analyte. The strip contains, integral therewith, a second sbp member for concentrating and non-diffusively binding the first sbp member at a small situs on the strip separate from an end portion of the strip provided for contacting with the test solution. Generally, the second sbp member binds to a complex formed from the binding of the analyte to the first sbp member. A detectible signal is produced by means of a signal producing system. The signal is produced in relation to the presence of analyte in the test solution. In one embodiment an analog of the analyte is non-diffusively bound to the strip at least between the situs and the portion of the strip that contacts the test solution.

In the method an end portion of the strip separated from the situs is contacted with the test solution, which traverses the bibulous material by means of capillary action. The strip is contacted with a developer solution containing members of the signal producing system and then with any remaining members of the signal producing system that were not included in the test solution or the developer solution, or present initially on the strip. At least a portion of the test solution contacts the situs prior to contact of the developer solution with the situs. The signal detectible at the situs is then compared with the signal detectible at a portion of the strip other than at the situs to determine the presence of the analyte in the test solution.

In a particular embodiment of the present invention the signal produced at the small situs has a sharp-edged distinctive pattern that provides a sharp contrast to the signal produced at portions of the strip other than at the situs when analyte is present in the test solution.

In another particular embodiment of the present invention, the second sbp member is non-diffusively bound to a small situs on the strip through the intermediacy of particles non-diffusively bound to the small situs. Where the second sbp member is able to bind the first sbp member when the first sbp member is not bound to the analyte an analog of the analyte capable of binding the first sbp member is non-diffusively bound to the strip between the situs and the end portion.

The method and device of the present invention have particular applicability to the determination of a plurality of analytes in a test solution. The presence or absence of one or more analytes in the test solution can be readily determined on a single strip. In addition, the method of the invention provides for the detection of analytes, such as drugs, without the need for reference materials or instrumentation.

DESCRIPTION OF THE SPECIFIC EMBODIMENTS

As mentioned above, the present invention is directed to methods and devices for determining the presence of an analyte in a sample suspected of containing the analyte. A test solution is formed by combining in an aqueous medium the sample and a first sbp member capable of binding the analyte. The end portion of a strip of bibulous material capable of being traversed by this test solution by means of capillary migration is contacted with the test solution. The strip contains, integral therewith, a second sbp member capable of binding the complex formed from the analyte and the first sbp member. The second sbp member is non-diffusively bound at a small situs on the strip separate from the end portion. The test solution is allowed to traverse at least a portion of the strip. Next, the strip is contacted with a developer solution containing members of the signal producing system. In the method at least a portion of the test solution contacts the situs prior to contact of the situs with the developer solution. The strip is then contacted, where necessary, with any remaining members of the signal producing system that were not included in the test solution or the developer solution or present on the strip. The detectible signal at the situs is then compared with the signal detectible at a portion of the strip other than at the situs. A signal is produced at the situs in relation to the presence of analyte in the test solution.

The second sbp member provides a means for concentrating and non-diffusively binding the first sbp member to the strip at the situs. The first sbp member is part of a signal producing system which provides a detectible signal at the situs in relation to the amount of analyte in the sample. The surface area of the situs is substantially less than that of the strip. The second sbp member has the characteristic of binding a complex of the first sbp member by binding directly to the analyte, by binding directly to the first sbp member, including binding to the signal generating label, or by binding at a site that is present only in the complex. Where the second sbp member is able to bind the first sbp member directly and is therefore able to bind uncomplexed first sbp member, an analyte analog capable of binding uncomplexed first sbp member is bound to the strip. The analyte analog normally is non-diffusively bound to the strip at least between the situs and the end portion.

The means for producing a detectible signal is usually a signal producing system having one component conjugated to an sbp member to provide a label-sbp member conjugate. The amount of label producing the detectible signal is related to the amount of analyte in the test solution. The signal producing system comprises the label-sbp member conjugate and all other reagents required to produce a detectible signal at the situs in relation to the presence or amount of analyte in the sample.

In a particular embodiment of the present invention the second sbp member is conjugated to particles, which particles are non-diffusively bound to the strip at the situs.

The small situs can be a band running transverse to the direction of traversal of the test solution alone the strip. The signal produced at the small situs can have a sharp-edged distinctive pattern that provides a sharp contrast to signal produced at a portion of the strip other than the situs. Usually, the signal generated at the small situs is compared with adjacent areas on the strip.

The present invention is particularly applicable to the determination of the presence of a plurality of analytes in a test solution.

Before proceeding further with the description of the specific embodiments of the present invention, a number of terms will be defined.

Analyte—the compound or composition to be measured, which is a member of a specific binding pair and may be a ligand, which is mono- or poly-valent, usually antigenic or haptenic, a single or plurality of compounds which share at least one common epitopic or determinant site, or a receptor.

The polyvalent ligand analytes will normally be poly (amino acids), i.e., polypeptides and proteins, polysaccharides, nucleic acids, and combinations thereof. Such combinations include bacteria, viruses, chromosomes, genes, mitochondria, nuclei, cell membranes and the like.

The precise nature of the analytes together with numerous examples thereof are disclosed in U.S. Pat. 4,299,916 to Litman, et al., particularly columns 16 to 23, the disclosure of which is incorporated herein by reference.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair, although other specific binding pairs such as biotin-avidin, hormones-hormone receptors, nucleic acid duplexes and the like are not immunological pairs.

Ligand—any organic compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component Clq, and the like.

Ligand analog or analyte analog—a modified ligand or ligand surrogate or modified analyte or analog surrogate which can compete with the analogous ligand or analyte for a receptor, the modification providing means to join a ligand analog or analyte analog to another molecule. The ligand analog or analyte analog will usually differ from the ligand or analyte by more than replacement of a hydrogen with a bond which links the ligand analog or analyte analog to a hub or label, but need not. The term ligand surrogate or analyte surrogate refers to a compound having the capability of binding the first sbp member. Thus, the ligand surrogate or analyte surrogate may bind to the first sbp member in a manner similar to the ligand or analyte. On the other hand, the surrogate could be, for example, an antibody directed against the idiotype of an antibody to the ligand or analyte.

Bibulous material—a porous material having pores of at least 0.1μ, preferably at least 1.0μ, which is susceptible to traversal by an aqueous medium in response to capillary force. Such materials are generally hydrophilic or are capable of being rendered hydrophilic and include inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, etc.; either used by themselves or in conjunction with other materials; ceramic materials; and the like. The bibulous material can be attached to a support. On the other hand, the bibulous material may provide its own support. The bibulous material may be polyfunctional or be capable of being polyfunctionalized to permit covalent bonding of sbp members as well as to permit bonding of other compounds which form a part of the signal producing system.

Binding of sbp members to the bibulous material may be accomplished by well-known techniques, commonly available in the literature. See, for example, "Immobilized Enzymes," Ichiro Chibata, Halsted Press, New York (1978) and Cuatrecasas, *J. Bio. Chem.*, 245:3059 (1970).

The bibulous material can be a single structure such as a sheet cut into strips or it can be particulate material bound to a support or solid surface such as found, for example, in thin-layer chromatography.

The support for the bibulous material where a support is desired or necessary will normally be water insoluble, non-porous, and rigid and usually will be of the same length and width as the bibulous strip but may be larger or smaller. A wide variety of organic and inorganic materials, both natural and synthetic, and combinations thereof, may be employed provided only that the support does not interfere with the capillary action of the strip, or non-specifically bind assay components, or interfere with the signal producing system. Illustrative polymers include polyethylene, polypropylene, poly(4-methylbutene), polystyrene, polymethacrylate, poly(ethylene terephthalate), nylon, poly(vinyl butyrate), glass, ceramics, metals, and the like.

Labeled-sbp member—a label, for example, a catalyst, usually an enzyme, conjugated to an sbp member, which is a member of the signal producing system. The sbp member can bind directly to the analyte or can bind indirectly to the analyte by binding to an sbp member complementary to the analyte.

Label—A label may be any molecule conjugated to another molecule or to the bibulous support and, where two molecules are involved, is arbitrarily chosen as to which molecule is the label. In the subject invention, the labels will be a member of the signal producing system that is conjugated to an sbp member. The label may be isotopic or nonisotopic, preferably nonisotopic. However, an isotopic label can be preferred for achieving high sensitivity when using radio-autographic detections with photographic film.

Signal Producing System—The signal producing system may have one or more components, at least one component being the label conjugated to an sbp member. The signal producing system includes all of the reagents required to produce a measurable signal. When the first sbp member is not conjugated to a label, the label is normally bound to an sbp member complementary to the first sbp member and is usually included as part of the developer. Other components of the developer include substrates, coenzymes, enhancers, second enzymes, activators, cofactors, inhibitors, scavengers, metal ions, specific binding substances required for binding of signal generating substances, and the like. The components of the signal producing system may be bound to the strip such as coenzymes, substances that react with enzymic products, other enzymes and catalysts, and the like. The signal producing system provides a signal detectable by external means, normally by measurement of electromagnetic radiation, desirably by visual examination. For the most part, the signal producing system includes a chromophoric substrate and enzyme, where chromophoric substrates are enzymatically converted to dyes which absorb light in the ultraviolet or visible region, phosphors or fluorescers.

The signal-producing system can include at least one catalyst, usually at least one enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal at the small situs, related to the amount of catalyst bound to the situs, as a result of sbp member complex formation of the labeled sbp member.

The signal producing system provides for the production of a compound, which is normally the signal generating compound, but in some instances may react with another compound bound to the surface with the production, enhancement or destruction of the signal generating compound. While both enzymatic and non-enzymatic catalysts may be employed, usually there will be at least one enzyme catalyst employed in the signal producing system. In the event of there being only one catalyst, this catalyst will usually be conjugated to an sbp member for binding to the situs through sbp member complex formation. In addition to the catalyst, there must be a substrate which undergoes a transformation which results in a change in a detectable signal at the measurement surface. For the most part, the product resulting from the transformation catalyzed by the labeled sbp member will be the signal generating compound.

Two catalysts may be employed, either a combination of an enzyme and a non-enzyme catalyst or two enzymes, where the two catalysts are related in that the product of one is the substrate of the other. In this system, there need be only one substrate which can undergo successive changes catalyzed by the catalysts, which results in the compound involved with production of a detectable signal. For the most part, however, there will normally be a substrate for the first enzyme in the series and a second compound, which serves as a precursor to the compound involved in the production of the signal, normally providing the compound which produces the signal. Thus, the product of the first enzyme may react with the precursor to the signal producing compound to provide the signal generating compound.

For the most part, the involved reactions will be hydrolysis or redox reactions. In the case of hydrolysis, a derivatized dye precursor that has an enzymatically labile bond and an enzyme that catalyzes its conversion to an insoluble dye product, is illustrative of this type of system. In redox reactions, a first enzyme would produce an essential oxidizing substrate required for the second enzyme, where the second enzyme catalyzes the reaction between the oxidizing substrate and a dye precursor.

Where two enzymes are used, the first enzymatic reaction may involve hydrolytic cleavage or a redox reaction of the substrate to provide a product which is the substrate of another enzyme. The first situation may be illustrated by glucose-6-phosphate being catalytically hydrolyzed by alkaline phosphatase to glucose, where glucose is a substrate for glucose oxidase. The second situation may be illustrated by glucose being oxidized by glucose oxidase to provide hydrogen peroxide which would enzymatically react with a leuco dye to produce a signal generator.

Coupled catalysts can also involve an enzyme with a non-enzymatic catalyst. The enzyme can produce a reactant which undergoes a reaction catalyzed by the non-enzymatic catalyst or the non-enzymatic catalyst may produce a substrate (includes coenzymes) for the enzyme. A wide variety of non-enzymatic catalysts which may be employed are found in U.S. Pat. No. 4,160,645, issued Jul. 10, 1979, the appropriate portions of which are incorporated herein by reference.

Various combinations of enzymes may be employed to provide a signal generating compound. Particularly, combinations of hydrolases may be employed to produce an insoluble signal generator. Alternatively, combinations of hydrolases and oxidoreductases can provide the signal generating compound. Also, combinations of oxidoreductases may be used to produce an insoluble signal generating compound.

For combinations of enzymes one enzyme can be non-diffusively bound to the strip, while the other enzyme is conjugated to a sbp member. Additionally, one or more other members of the signal producing system can be bound to the strip depending on the particular signal producing system chosen or the particular protocol followed.

In order to have a detectable signal, it is desirable to provide means for amplifying the signal produced by the presence of the label bound at the situs. Therefore, it will usually be preferable for the label to be a catalyst or luminescent compound or radioisotope, most preferably a catalyst. Preferably catalysts are enzymes and coenzymes which can produce a muliplicity of signal generating molecules from a single label.

An enzyme or coenzyme is employed which provides the desired amplification by producing a product, which absorbs light, e.g., a dye, or emits light upon irradiation, e.g., a fluorescer. Alternatively, the catalytic reaction can lead to direct light emission, e.g., chemiluminescence. A large number of enzymes and coenzymes for providing such products are indicated in U.S. Pat. No. 4,275,149 bridging columns 19 to 23, and U.S. Pat. No. 4,318,980, columns 10 to 14, which disclosures are incorporated herein by reference.

Of particular interest is the use of a combination of enzymes, where the enzymes are related by the product of one enzyme being the substrate of the other enzyme. In this manner, stable precursors to labile substrates can be provided and the substrate for a second enzyme can be stored in combination with a first enzyme without a reaction being prematurely initiated.

A number of enzyme combinations are set forth in U.S. Pat. No. 4,275,149, bridging columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference. When a single enzyme is used as a label, other enzymes may find use such as hydrolases, transferases, and oxidoreductases, preferably hydrolases such as alkaline phosphatase and β-galactosidase. Alternatively luciferases may be used such as firefly luciferase and bacterial luciferase.

Illustrative coenzymes which find use include NAD[H]; NADP[H], pyridoxal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

Ancillary Materials—Various ancillary materials will frequently be employed in the assay in accordance with the present invention. For example, buffers will normally be present in the assay medium, as well as stabilizers. Frequently, in addition to these additives, additional proteins may be included, such as albumins, or surfactants, particularly non-ionic surfactants, binding enhances, e.g., polyalkylene glycols, or the like.

Small situs—an area on the strip of bibulous material which has a surface area substantially less than the surface area of the strip. The situs may be a dot, line, curve, band, pattern formed from dots, lines, curves, bands, or combinations thereof, or the like. Generally, the direction of traversal of the strip by the test solution will be transverse to the situs. Preferably, the signal produced at the situs has a sharp-edged distinctive pattern that provides a sharp contrast to signal produced at portions of the strip other than the situs. For example, the situs can be a printed display of an abbreviated name or names of the analyte or analytes in the test solution, of a plus signs or of the like. The situs is separated from the end portion of the strip contacted with the test solution in accordance with the concentrating principle of the present invention. The situs should contact a major portion of the solution flowing through the strip for efficient concentration.

In the method of the invention, a first sbp member capable of binding to the analyte is combined with a sample suspected of containing the analyte to provide an aqueous test solution. A second sbp member capable of binding the complex formed upon binding of the analyte to the first sbp member is non-diffusively bound to the bibulous strip at the small situs. One end of the strip is contacted with the test solution, which will traverse the strip through capillary action. The amount of the first sbp member that becomes bound to the situs through binding to the second sbp member is related to the amount of analyte in the sample. The signal producing system provides a detectible signal at the situs only when the first sbp member is bound, so that the presence of the analyte may be determined by comparing the signal detectible at the situs with the signal detectible at a portion of the strip other than at the situs, usually a portion of the strip adjacent to the situs. The first sbp member binds specifically to the analyte. The second sbp member is non-diffusively bound at the situs and is able to bind the first sbp member. Binding may occur directly to a binding site on the first sbp member, or indirectly to a binding site on the analyte which is bound to the first sbp member. Binding may also occur at a site characteristic of the complex of the analyte and first sbp member which site is not present in either component alone.

Where binding of the first sbp member to the second sbp member occurs directly, it is necessary to provide for removal of free first sbp member by providing an analog of the analyte non-diffusively bound to the strip at least between the situs and the end portion. A second sbp member will normally be chosen that provides for direct binding to the first sbp member when the analyte has a single binding site, e.g., a drug, or when only one sbp member complementary to the analyte is available. Generally, the amount of analog analyte bound to the strip should be sufficient to bind all of the first sbp member when no analyte is present in the test solution. Usually, such analog will be present in an excess amount.

The movement of the test solution along the strip is due to capillarity. This capillary movement along the strip causes the test solution to be carried through the situs. Preferably after the strip has been contacted with the test solution, a developer solution provides for continuation of the capillary migration through the situs. In this instance the developer solution is contacted with the end portion of the strip which was contacted with the test solution. Alternatively, to contact the strip with the developer solution, the situs can be immersed in the developer solution after the end portion of the strip has been contacted with the test solution. In any event one desires to provide concentration of the first sbp member at the situs prior to contact of the situs with the developer.

The solvent will normally be an aqueous medium, which may be up to about 40 weight percent of other polar solvents, particularly oxygenated solvents of from 1 to 6, more usually of from 1 to 4 carbon atoms, including alcohols, ethers and the like. Usually, the cosolvents will be present in less than about 20 weight percent.

The pH for the medium will usually be in the range of 4–11, more usually 5–10, and preferably in the range of about 6–9. The pH is chosen to maintain a significant level of binding affinity of the sbp members and optimal generation of signal by the signal producing system. Various buffers may be used to achieve the desired pH and maintain the pH during the assay. Illustrative buffers include borate, phosphate, carbonate, tris, barbital and the like. The particular buffer employed is not critical, but in individual assays, one buffer may be preferred over another.

Desirably, from about 0.05 to 0.5 wt. % of a non-ionic detergent is included with the sample. Various polyoxyalkylene compounds may be employed of from about 200 to 20,000 daltons.

Moderate, and desirably substantially constant, temperatures are normally employed for carrying out the assay. The temperatures for the assay and production of a detectable signal will generally be in the range of about 4°–50° C., more usually in the range of about 10°–40° C., and frequently will be ambient temperatures, that is, about 15°–25° C.

The concentration, in the liquid sample, of analyte which may be assayed will generally vary from about $10^{-4}$ to about $10^{-5}$M, more usually from about $10^{-6}$ to $10^{-14}$M. Considerations, such as the concentration of the analyte of interest and the protocol will normally determine the concentration of the other reagents.

While the concentrations of many of the various reagents in the sample and reagent solutions will generally be determined by the concentration range of interest of the analyte, the final concentration of each of the reagents will normally be determined empirically to optimize the sensitivity of the assay over the range of interest. With certain protocols, individual reagents may be used in substantial excess without detrimentally affecting the sensitivity of the assay.

The size of the strip is dependent on several considerations. When capillary flow is predominantly upward, the length and thickness of the strip control, the amount of solution that can pass through the situs. The transfer of a large volume of first solution requires that the fluid capacity of the strip above the situs be sufficient to accommodate the desired volume. If the strip is used to provide a predominantly downward flow so as to syphon the test solution this volume requirement is not needed. Moreover, if an absorbant material is provided to contact the end of the strip not used to contact the test solution the volume requirement is also eliminated. In general, it is desirable to transfer as large a volume as possible through the situs so as to provide the greatest assay sensitivity. However, other considerations such as time and the availability of the sample will limit this requirement. In general, for upward flow strips the fluid retention volume about the situs will be usually greater than 20 µL, preferably at least 50–200 µL. For downward flow strips retention volumes as low as 2–20 µL can be used but volumes of 20–200 µL are preferable.

Thickness of the strips will usually be no greater than 20% of the width, preferably 1 to 10%, more preferably 2 to 5%.

To permit conservation of reagents and provide for samples of limited size, the width of the strip will generally be relatively narrow, usually less than 20 mm, preferably less than 10 mm. Generally, the width of the strip will not be less than about 1.0 mm and will usually range from about 2 mm to 12 mm, preferably from about 4 mm to 8 mm.

The length of the strip will depend on the concentration of the analyte and practical considerations such as ease of handling and the number of situses on the strip and will be about 2 cm to 40 cm, usually about 4 cm to 25 cm, preferably about 6 to 20 cm but may be of any practical length. The structure of the strip can be varied widely and includes fine, medium fine, medium, medium coarse and coarse. In general, smaller pore size and finer material will provide slow capillary flow and efficient capture of binding sbp members on the strip. Courser, more porous materials provide faster flow, but the efficiency of capture is reduced. Selection of the porosity of the material depends on the rate of binding of the sbp members for a given assay.

The position of the small situs, or small situses where a plurality of analytes are being determined, should be governed by the basic principle involved in the present invention. One desires to pass by capillarity a sufficient amount of the test solution through the situs to concentrate a sufficient amount of the analyte at the situs to produce a signal that is detectible over the background. Thus, it is desirable to position the situs close to the end of the strip which is to contact the test solution but not so close as to come into contact with the bulk solution or the meniscus. Desirably, the situs should be at least 5 mm, preferably at least 8 mm, from such end of the strip. It may be positioned any greater distance away from the end provided the test solution can pass through the situs by capillary action. Preferably, the situs will not be greater than half the length of the strip from such end. In this way, the situs is "separated" from such end portion. Where several situses are used, the situses can be grouped close together or apart but must not be so close as to compromise resolution of the signal. Consequently, such situses usually should be spaced not less than 1 mm apart, preferably at least 3 mm apart.

Other reagents which are members of the signal producing system can vary widely in concentration depending upon the particular protocol and their role in signal production. Usually the first sbp member will not exceed $10^4$ times the maximum concentration of interest of the analyte when the analyte has multiple binding sites and will not exceed $10^3$ times the maximum concentration of interest when a monovalent analyte is used. Normally, the first sbp member will not be less than about 0.5 times the minimum concentration of interest. When the label is not bound directly to the first sbp member, the reagent to which it is bound must bind to the first sbp member and will be present in at least an amount equivalent to the lowest concentration of interest of the analyte.

In carrying out the assay, the protocol will normally involve combining the sample suspected of containing the analyte with the first sbp member to form the aqueous test solution. The sample may be derived from a wide variety of sources, such as physiologic fluids, illustrated by saliva, blood, serum, plasma, urine, ocular lens fluid, spinal fluid, etc., chemical processing streams, food waste water, etc.

The end portion of the strip, usually, the end closest to the situs, is contacted with the test solution, usually by immersion of the end portion into the test solution. Wetting of the strip by capillary action usually is allowed to continue at least until the situs is wet. Preferably, at least half the strip is wet with the test solution. When downward syphoning flow is used, usually the entire strip will be wet and excess test solution can be allowed to syphon through the strip.

For the most part, relatively short times are involved for the test solution to traverse the strip. Usually, the traverse of the test solution over the strip will take at least 30 sec and not more than 1 hour, more usually from about 1 min to 30 min. The development of the signal will generally range from 30 sec to 30 min, more usually from about 30 sec. to 5 min.

After the liquid has traversed at least a portion of the strip, the strip is contacted with a developer solution having members of the signal producing system. This may be accomplished by immersion of the strip into the developer solution, but preferably only the end of the strip previously in contact with the test solution is contacted with the developer solution. Where the test solution contains unlabeled first sbp member, the developer solution will have a labeled sbp member that can bind to the complex formed between the first sbp member and the analyte. Upon contact of the end portion of the strip with the developer solution, the solution traverses the strip by capillary action at least to the small situs and preferably until the entire strip is wet.

When an enzyme is used as a label, the substrate will normally be in substantial excess, so as not to be rate limiting (greater concentration than Km). The developer solution will usually be appropriately buffered for the enzyme system.

After contacting the strip with the developer solution, the strip is contacted with any remaining members of the signal producing system not present in the developer or test solutions or present on the strip. A sufficient time is allowed to elapse prior to measuring the signal to produce an amount of the signal producing compound required to define the region of the situs in which the analyte is bound. Once the detectable signal has been produced, the presence or absence of the analyte or analytes in the sample is known.

The ligand analytes are characterized by having single binding sites (monovalent) or multiple binding sites (polyvalent), while the receptor analytes may also have a single or plurality of binding sites. The polyvalent analytes will normally be poly(amino acids), i.e., polypeptides and proteins, polysaccharides, nucleic acids, and combinations thereof. Such combinations or assemblages include bacteria, viruses, chromosomes, genes, mitochondria, nuclei, cell membranes and the like.

For the most part, the polyvalent ligand analytes will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight, and among hormones of interest, about 5,000 to 60,000 molecular weight.

An extensive listing of useful ligands may be found in U.S. Pat. No. 4,275,149, the disclosure bridging columns 12 to 17, which disclosure is incorporated herein by reference.

The monovalent ligand analytes will generally be from about 100 to 2,000 molecular weight, more usually from about 125 to 1,000 molecular weight. The analytes of interest include drugs, hormones, metabolites, pesticides, pollutants, and the like.

A large number of analytes of interest are listed in U.S. Pat. No. 4,275,149, columns 17 and 18, which disclosure is incorporated herein by reference.

For receptor analytes, the molecular weights will generally range from about $10^4$ to $2 \times 10^8$ more usually from about $3 \times 10^4$ to $2 \times 10^6$. For immunoglobulins, e.g., IgA, IgD, IgE, IgG and IgM, the molecular weights will generally vary from about 160,000 to about $10^6$. Enzymes will normally vary from about 10,000 to 600,000 daltons. Natural receptors vary widely, being generally at least about 25,000 molecular weight and may be $10^6$ and higher, including such materials as avidin, thyroxine binding globulin, thyroxine binding prealbumin, transcortin, membrane surface proteins, etc.

Where a ligand is conjugated to another molecule or support, frequently the ligand will be modified to provide for a particular functional group at a particular site. This modification produces a product referred to as a ligand analog. U.S. Pat. No. 4,275,149 also has an extensive description of ligand analogs, bridging columns 18 and 19, which description is incorporated herein by reference.

The strip can be coated with a wide variety of materials to provide for enhanced properties. Coatings may include protein coatings, polysaccharide coatings, synthetic polymers, sugars or the like, which are used particularly to enhance the stability of the materials conjugated to the support. These compounds can also be used for improved binding of the materials, such as the sbp member or signal producing system member bound to the strip.

The strip, or the situs, can be activated with reactive functionalities to provide for covalent bonding of the organic materials to be conjugated to the strip such as those described in U.S. Pat. No. 4,168,146.

The amount of sbp member which is bound to the strip at the situs will vary depending upon the amount required to bind all of the labeled sbp member. Generally, the amount of sbp member at the situs will be at least equivalent to the amount of analyte that flows through the situs and can exceed the amount of analyte by ten thousand fold or more.

The second sbp member, the analyte analog, and, where desired, members of the signal producing system can be bound to the strip by adsorption, rather than covalent bonding, as long as such binding is non-diffusive. This will involve contacting the bibulous support with a solution containing the materials to be bound to the strip and allowing the strip to dry. In general, this procedure will be useful only where the bibulous support is relatively hydrophobic or has a high surface charge, and subsequent treatment with proteins, detergents, polysaccharides, or other materials capable of blocking non-specific binding sites will be required.

In a preferred embodiment of the invention the first sbp member can be non-diffusively bound to particles or beads. The particles or beads can then be applied to the strip at the situs. Generally, the particles will have means for specifically binding a labeled sbp member or a label without significant non-specific interaction. The nature of the particle or the beads may vary widely, being naturally occurring or synthetic. The materials are commercially available or commercially available materials may be modified. Exemplary of such particles or beads are latex particles made from polystyrene, polyacrylates, polyacrylamide, available as Biogel-p®, or naturally occurring materials such as polysaccharides, particularly cross-linked polysaccharides, such as agarose, which is available as Sepharose®, dextran, available as Sephadex®, microcrystalline cellulose, starch and the like. Other materials include polyacrylamides, polystyrene, polyvinyl alcohol, copolymers of hydroxyethyl methacrylate and methyl methacrylate, silicones, glasses, available as Bioglas®, diatomaceous earth, silica, and the like. The primary requirement is that the materials do not contribute a signal, usually light absorption, that would cause the situs to have a different signal than other parts of the strip prior to contact with the signal producing system.

The particles must be capable of non-diffusivable attachment to an sbp member where the attachment can be achieved by covalent or non-covalent binding. When the sbp member is covalently bound, the particles should be polyfunctional or be capable of being polyfunctionalized. A wide variety of functional groups are available or can be incorporated. Functional groups include carboxylic acids, aldehydes, amines, amides, activated ethylenes such as maleimide, hydroxyls, sulfonic acids, mercaptans, and the like. The manner of linking a wide variety of compounds to the various particles is well known and is amply illustrated in the literature. See, for example, Cautrecases, *J.Biol.Chem.* 245, 3059 (1970).

The length of the linking groups will vary widely depending upon the nature of the compound being linked, the effect of distance between the label and the particle on the label's properties, the potential for cross-linking of the labels, and the like.

The particles should not migrate to any significant degree. The size of the particles can vary but must be of a size to infiltrate the pores of the bibulous material and become imbedded or non-diffusively bound therein. Thus, the particles are generally slightly larger than the minimum size of the pores of the bibulous material and smaller than the maximum pore size. Usually, the size of the particles will range from about 0.1 to 50 microns, more usually from about 0.4 to 10 microns, preferably greater than 0.5μ.

Particles having a non-diffusively bound sbp member may be used to non-diffusively bind the sbp member to the strip at a small situs with sharply defined edges. Several methods may be employed. Usually a suspension of the particles in a liquid, that frequently is aqueous, will be applied to the strip. Application may be by any standard printing process including the use of electrostatic and laser propelled jets, and printing probe or type face. In addition, particles could be applied by template. The shape of the situs would be defined by a cut pattern through which particles would be absorbed into the bibulous strip. Alternatively, the suspension can be transferred to the strip by inscribing with a pen or microcapillary tube. Where dry particles are used, they may be applied by directing a jet of a suspension of the particles in a gas, usually air, at the desired situs. In each case, particularly when printing techniques are not used, it will frequently be desirable to provide for reduced pressure on the side of the strip opposite to the side used to apply the particles. Pressure reduction is conveniently provided by placing a sheet of the bibulous material on a filter or porous plate that covers a vacuum chamber. The suspension is then applied while air is being drawn through the material. Regardless of the method of application of the particles it is usually preferable to wash the situs free of unbound particles after they have been applied.

The liquid used to suspend the particles will usually be aqueous and must not dissolve the particles or damage or release the bound sbp member. Thickners and surfactants may be added to limit capillary flow and provide sharply defined edges. Thickners may include polyvinyl alcohol, polypyrolidone, dextran, glycerol, and the like. Surfactants may be ionic, usually anionic, or non-ionic.

A variety of embodiments of the present invention will next be described in some detail. In one embodiment, the analyte in the sample is polyvalent. A second sbp member which recognizes a determinant site on the analyte is non-diffusively bound at a small situs on the strip of bibulous material. The non-diffusive binding may be accomplished by any of the means described hereinabove. A test solution having a volume approximately equal to the fluid capacity of the strip is prepared by combining the sample which is suspected of containing the analyte and a labeled first sbp member wherein the latter sbp member binds to a determinant site on the analyte to form a complex. The end portion of the bibulous strip nearest the situs is contacted with the test solution, which is allowed to traverse the bibulous strip by means of capillary action. The test solution moves along the strip and through the situs until the entire strip is wet or the test solution is exhausted. The complex of the analyte and labeled first sbp member binds to the second sbp member at the situs, thereby concentrating the labeled first sbp member at the situs. After the test solution is allowed to traverse the bibulous strip, the strip is then contacted with a developer solution containing the remaining members of the signal producing system of which the label is one member. If the analyte is present in the test solution, a signal will be produced at the small situs. This signal can be distinguished from signal generated adjacent to the situs.

In a variant of the above-described embodiment, the volume of the test solution is sufficient to permit it to traverse only a portion of the strip such that the fluid capacity at the dry portion of the strip is at least as great as the fluid capacity of the portion from the end portion through the small situs. The end portion of the strip, which end portion was previously contacted with the test solution, is next contacted with the developer solution. The developer solution moves along the strip through the small situs by capillarity. In doing so, the developer solution causes the remainder of the test solution to move through the small situs. If analyte is present in the test solution, a signal is generated.

In another variant of the above-described embodiment the first sbp member is not labeled. The assay is carried out in the same way but a labeled sbp member complementary to the first sbp member is included in the developer. When analyte is present, the first sbp member binds to the situs and thereby causes binding of the labeled sbp member to the situs. In this embodiment, it is often preferable to exclude some members of the signal producing system from the developer and to contact the strip with a solution containing these excluded, i.e., remaining, members after contact with the developer.

In the above embodiment, a plurality of polyvalent analytes may be determined. To this end, several situses separated from the end portion are employed. At one situs a second sbp member which recognizes a determinant site on a first analyte is non-diffusively bound to the bibulous strip. At another situs another second sbp member which recognizes a determinant site on a second analyte is non-diffusively bound. The situation continues until there is a small situs for each of the analytes for which one desires to test. The sample to be analyzed is then combined in an appropriate aqueous medium with a plurality of labeled first sbp members to form the test solution. One labeled first sbp member will contain an sbp member which recognizes a determinant site on the first analyte other than the determinant site recognized by the second sbp member on the bibulous strip which binds to the first analyte. Another labeled first sbp member will contain an sbp member which recognizes a determinant site on the second analyte other than the determinant site recognized by the second sbp member on the bibulous strip which binds to the second analyte. The number of labeled sbp members will correspond to the number of analytes for which one desires to test. If the analyte or analytes tested for are present in the sample, a complex of each respective analyte with its corresponding labeled first sbp member is formed. If the analyte is not present, then no such complex forms. The end portion of the bibulous strip is contacted with the test solution, which is allowed to traverse the strip. Any complexes of analyte and labeled sbp member will bind to the respective situses on the strip. If the analyte is not present, no complex forms and, therefore, the labeled first sbp member which corresponds to that analyte does not become bound at the situs and a signal will not be produced. After the test solution has traversed the bibulous strip, the strip is contacted with the appropriate members of the signal producing systems employed. The assay may be designed so that a single developer is employed for all of the analytes for which one desires to test. If the particular analyte is present in the sample, a signal will be produced at the appropriate situs. In a particularly preferred variant of this procedure, the first sbp members are not labeled, and the developer contains a labeled sbp member complementary to the first sbp members. The strip is contacted with the remaining members of the signal producing system following contact with the developer.

In another embodiment of the present invention, the analyte is a monovalent drug. The sample suspected of containing the drug is mixed with a labeled first sbp member in an appropriate medium to form the aqueous test solution. The labeled first sbp member binds to the drug. The bibulous strip will contain a second sbp member at the small situs, which sbp member recognizes a determinant site on the labeled first sbp member other than the determinant site involved in the binding of the labeled sbp member to the drug. For example, the second sbp member may recognize a determinant site on the label portion of the labeled first sbp member or on the sbp member portion. In this particular embodiment, an analyte or drug analog must be bound to the strip in an amount at least sufficient to bind all of the labeled sbp member when drug is absent in the sample tested. Usually, this analyte analog is a derivative of the drug tested for and is bound to the strip in a substantial excess at least between the end portion of the strip and the situs. Although it is preferred that this drug analog be a derivative of the drug, one may use other drug analogs such as, for example, an antibody directed against the idiotype of an antibody to the drug. When the sample and the labeled first sbp member are mixed together to form the test solution and the drug is present in the sample, a complex between the drug and the labeled first sbp member is formed. This complex of drug and labeled first sbp member moves along the bibulous strip until it reaches the situs to which it becomes bound due to binding with a second sbp member specific for the labeled first sbp member at the situs. If the drug is not present in the sample, then no complex is formed between the drug and the labeled first sbp member. When the test solution is contacted with the end portion of the bibulous strip, the labeled first sbp member that is not complexed with the drug binds to the drug analog which is non-diffusively bound to the strip. Since this drug analog is present in excess quantity, the uncomplexed labeled sbp member does not reach the small situs. In subsequent development of the test strip, the presence of drug in the sample will be indicated by production of a signal at the small situs.

In the latter embodiment for monvalent drugs, one may also assay a test solution for a plurality of drugs. In this situation the test solution is formed by mixing together in an appropriate liquid medium the sample and a number of labeled first sbp members corresponding to the number of analytes for which one desires to test. If it is only desired to know if any one of the drugs is present, the bibulous strip contains a situs identical to that described above for a single drug. It is necessary, however, to include on the strip drug analogs corresponding to each one of the drug for which one is testing. If it is necessary to know which drugs are present, the strip contains a separate situs for each drug on which situs is bound a second sbp member that specifically binds to a determinant site that is characteristic of the labeled first sbp member corresponding to that drug. A provision for a characteristic determinant site is preferably made by attaching a hapten to the labeled first sbp member and using an antibody to the hapten as the second sbp member.

As a matter of convenience, the present device can be provided in a kit in packaged combination with predetermined amounts of reagents for use in assaying for an analyte. Where an enzyme is used as the label, the reagents will include enzyme labeled first sbp member, substrate for the enzyme or precursors therefor including any additional substrates, enzymes and cofactors and any reaction partner of the enzymic product required to provide the detectable chromophore or fluorophore. In addition, other additives such as ancillary reagents may be included, for example, stabilizers, buffers, and the like. The relative amounts of the various reagents may be varied widely, to provide for concentrations in solution of the reagents which substantially optimize the sensitivity of the assay. The reagents can be provided as dry powders, usually lyophilized, including excipients, which on dissolution will provide for a reagent solution having the appropriate concentrations for performing the assay.

EXAMPLES

The invention is demonstrated further by the following illustrative example. Before proceeding with a description of the illustrative example, a number of terms will be defined.

PBS: phosphate buffered saline
DMF: dimethyl formamide
BSA: bovine serum albumin
HCG: human chorionic gonadotropin
HRP: horseradish peroxidase
$PO_4$: mono- and dibasic phosphate, sodium salt
EDTA ethylenediaminetetraacetic acid
SAMSA: S-acetyl mercaptosuccinic anhydride
SMCC succinimidyl 4-(N-maleimido methyl) cyclohexane-1-carboxylate

| Phosphate Buffer: | 10 mN $PO_4$, pH = 7.40 |
|---|---|
| PBS: | 10 mM $PO_4$, pH = 7.40 |
| | 150 mM NaCl |
| Buffer A: | 10 mM $PO_4$, pH = 7.40 |
| | 150 mM NaCl |
| | 0.17, BSA |
| | 0.057, Tween −20 (Sigma Chemical Co.) |
| Conjugate Buffer: | 100 , $PO_4$, pH = 7.40 |
| | 150 mM NaCl |
| | 0.1% BSA |
| | 0.05% Tween −20 |
| Developer Buffer: | 10 mM $PO_4$, pH = 7.00 |
| | 20 mM NaCl |
| | 0.1% BSA |
| | 0.005% Triton QS −44 (Sigma Chemical Co.) |
| | 200 µg/ml 4-chloro-1-Naphthol |
| | 1 mM $H_2O_2$ |
| Carbonate Buffer: | 50 mM $Na_2CO_3$ pH = 9.50 |
| $PO_4$—NaCl-EDTA Buffer: | 100 mM Na $PO_4$ pH = 7.50 |
| | 100 mM NaCl |
| | 5 mM EDTA |
| Column Buffer: | 100 mM $Na_3PO_4$ pH = 7.00 |
| | 200 mM NaCl |
| | 0.02% $NaN_3$ |

Preparation of Conjugate of HRP and HCG Antibody

Preparation of HRP-SAMSA

Sixty (60) mg of HRP (Type VI, Sigma Chemical Co.) was dissolved in 2 ml of Carbonate Buffer and dialyzed to remove contaminants.

SAMSA (Sigma Chemical Co.) was made 100 mM in dry DMF. Thirty (30) mg of HRP was reacted with a twelve-fold molar excess of SAMSA for 1 hr. The product was purified from free SAMSA using a small Sephadex G-25 column equilibrated in $PO_4$—NaCl-EDTA Buffer.

To prepare free —SH groups from the SAMSA, the above product was incubated with a 1/10 volume of 1M $NH_2OH$ in PBS with stirring under Argon gas for 1 hr. The resulting product was purified on another Sephadex G-25 column and used immediately.

Preparation of Antibody-SMCC

Monoclonal antibody to the beta subunit of HCG was prepared according to the procedure of Kohler et al., Nature (1975) 265:495–497.

The antibody (4–5 mg/ml) was dialyzed against $PO_4$—NaCl-EDTA Buffer to remove contaminants. Following dialysis, 8 mg of antibody was reacted with a 25-fold molar excess of SMCC (Pierce Chemical Co.) for 2 hr. at room temperature with stirring. The SMCC was prepared fresh as a 100 mM solution in dry DMF.

The product was purified on a small Sephadex G-25 column and used immediately. The column was equilibrated with $PO_4$—NaCl-EDTA Buffer.

Conjugation Of HRP-SAMSA and Antibody-SMCC

The antibody-SMCC and a twelve-fold molar excess of HRP-SAMSA were combined and allowed to react at room temperature for 4 hr. with stirring. The reaction was quenched with 1 mM β-mercaptoethanol followed 15 minutes later by 2 mM N-ethylmaleimide.

Purification

The above conjugate was separated from free antibody and HRP by size exclusion chromatography on a Sephacryl S-300 column equilibrated with Column Buffer.

Preparation of Antibody-bound Beads

Polybead-carboxylate Microspheres, 3.92 µm diameter 2.5% suspension, from Polysciences, catalog number 9850, were employed. Four hundred (400) µl (10 mgs) of beads were washed with Phosphate Buffer and were suspended in 5 ml of a 2 mg/ml solution of Phosphate Buffer of a monoclonal antibody prepared in accordance with conventional techniques (Kohler, et al. Supra.). This monoclonal antibody recognizes only the alpha subunit of HCG.

The beads were incubated at room temperature overnight in the antibody solution with stirring to keep the beads suspended. The beads were then centrifuged, the antibody solution was decanted, and the beads were washed with 5 ml of each of Phosphate Buffer, PBS, and Buffer A.

After the wash with buffer A, the beads were suspended in 5 ml of PBS+10 mg/ml BSA (to block any non-specific binding) and mixed for 1 hour at room temperature.

Subsequently, the beads were centrifuged and then resuspended in 400 µl of Buffer A.

Preparation of Test Device

Whatman 31 ET paper which had been coated with a protein (polyclonal anti-theophylline) was used. The paper was cut into strips 6 mm wide and 9 or 18 cm long depending on the assay protocol. The paper strips were placed on a 4.5 cm diameter glass frit filter holder. Vacuum was applied and the strips were wetted with distilled water.

Ten (10) µl of the antibody-bound beads suspension prepared as described above (containing 250 µg beads) was absorbed into the paper by drawing a 5 µl capillary tube filled with the antibody-bound beads across the surface of the strip two times. The beads were then washed into the paper with 1 ml of Buffer A. The strips were allowed to dry on the vacuum.

ASSAY

A. One hundred (100) µl of HCG solution (20 ng/ml in Buffer A or in urine) was mixed with 100 µl HRP-HCG antibody conjugate solution (1/1000 diluted in Conjugate Buffer). A 2 mm portion of a Test Device (9 cm in length) was immersed in the above mixture, which was allowed to traverse the Test Device until the medium front reached the top of the Test Device. The Test Device then was immersed in 9 ml of Developer Buffer for 10 minutes and then was removed. A thin band of blue-gray color formed across the Test Device where the antibody-bound beads were located.

As a control the above procedure was repeated with the exception that 100 µl of Buffer A was employed in place of 100 µl of HCG solution. No color band appeared on the Test Device since HCG was not present in the test solution.

B. One hundred (100) µl of the HCG solution was mixed with 100 µl of HRP-HCG antibody conjugate solution. A 2 mm portion of a Test Device (18 cm in length) was immersed in the above mixture, which traversed the Test Device until the mixture was exhausted (about 10 min). A 2 mm portion of the same Test Device was further immersed in 200 µl of Developer Buffer, which was allowed to traverse the Test Device for about twenty more minutes. A thin band of blue-gray color formed across the Test Device where the antibody-bound beads were located.

As a control the above procedure was repeated with the exception that 100 μl of Buffer A was employed in place of 100 μl of HCG solution. No color band appeared on the Test Device since HCG was not present in the test solution.

The present invention provides a number of significant advantages over known methods. A primary advantage of the present invention is that a number of analytes can be determined in a single assay on a single test element. This provides a savings in operator's time and in cost. The reagents and devices can be manufactured easily and inexpensively which provides an additional cost savings. The assay result is determined by reference solely to the assay device and when the signal produced is a color or fluorescence, the device can be ready without the aid of an instrument. Therefore, a built-in control is provided. A positive result is easily distinguished over any background produced on the test device as the result of non-specific interactions. Also, the factors producing background signal affect the situs and the remaining area of the test device in substantially the same way.

Another advantage of the present invention is that cumbersome column techniques are avoided. The assay device is a bibulous strip that is easy to manipulate. A further advantage is that analyte is concentrated in a small zone, i.e., at the small situs. In many assay situations, the analyte is present in very small amounts, making detection difficult. Concentrating the analyte in a small zone enhances the accuracy of the determination particularly where the analyte is present in small amounts.

Another advantage of the present invention is that an excess of one of the sbp members, generally the labeled sbp member, can be employed. Using an excess of an sbp member aids in driving the reaction to produce the sbp member complexes.

Although the foregoing invention has been described in some detail by way of illustration and example for the purposes of clarity and understanding, it will be obvious that certain changes or modifications may be practiced within the scope of the appended claims.

What is claimed is:

1. A method for determining the presence of an analyte in a sample suspected of containing said analyte, which method comprises
   (a) providing in combination (1) a liquid medium containing said sample and a first sbp member and (2) a portion of bibulous material capable of being traversed by said liquid medium by capillary migration,
   said bibulous material containing a second sbp member non-diffusively bound to a small situs on said bibulous material separated from said portion, the surface area of said situs being substantially less than that of said bibulous material,
   said second sbp member having the characteristic of binding said first sbp member
   wherein a third sbp member capable of binding said first sbp member is non-diffusively bound to said bibulous material at least between said small situs and said portion,
   (b) allowing said liquid medium to traverse at least a portion of said bibulous material by means of capillary migration, and
   (c) detecting the presence or absence of the first sbp member at said situs.

2. The method of claim 1 wherein said bibulous material is in the form of a strip.

3. The method of claim 1 wherein said first sbp member is an antibody.

4. The method of claim 1 wherein second sbp member is non-diffusively bound to said small situs by virtue of particles non-diffusively bound to said bibulous material at said situs, said particles being conjugated to said second sbp member.

5. The method of claim 1 wherein said first sbp member is conjugated to a label.

6. The method of claim 5 wherein said first sbp member is detected at said situs by detecting said label.

7. The method of claim 1 wherein the analyte is a drug and said third sbp member is a drug analog which is non-diffusively bound to said bibulous material.

8. The method of claim 1 wherein the small situs is a band transverse to the direction of traversal of said liquid medium along said bibulous material.

9. The method of claim 1 for determining the presence of a plurality of analytes in said sample, wherein a plurality of corresponding second sbp members are each non-diffusively bound to a small situs on said bibulous material distant from said portion wherein each of said second sbp members is respectively capable of specifically binding a corresponding first sbp member and said first sbp members are provided in combination with said sample and said portion in said liquid medium.

10. A method for determining the presence of an analyte in a sample suspected of containing said analyte, which comprises
   (a) contacting, with a test solution containing said sample and a first sbp member, a contact portion of bibulous material capable of being traversed by said test solution by capillary migration,
   said bibulous material containing a second sbp member non-diffusively bound to a small situs on said bibulous material separate from said contact portion, the surface area of said situs being substantially less than that of said bibulous material,
   said second sbp member having the characteristic of binding said first sbp member
   wherein a third sbp member capable of binding said first sbp member is non-diffusively bound to said bibulous material at least between said small situs and said portion,
   (b) allowing said liquid medium to traverse at least a portion of said bibulous material by means of capillary migration, and
   (c) detecting the presence or absence of the first sbp member at said situs.

11. The method of claim 10 wherein said bibulous material is in the form of a strip.

12. The method of claim 10 wherein said first sbp member is an antibody.

13. The method of claim 10 wherein second sbp member is non-diffusively bound to said small situs by virtue of particles non-diffusively bound to said bibulous material at said situs, said particles being conjugated to said second sbp member.

14. The method of claim 10 wherein said first sbp member is conjugated to a label.

15. The method of claim 14 wherein said first sbp member is detected at said situs by detecting said label.

16. The method of claim 10 wherein the analyte is a drug and said third sbp member is a drug analog which is non-diffusively bound to said bibulous material.

17. The method of claim 10 wherein the small situs is a band transverse to the direction of traversal of said liquid medium along said bibulous material.

18. The method of claim 10 for determining the presence of a plurality of analytes in said sample, wherein a plurality of corresponding second sbp members are each non-diffusively bound to a small situs on said bibulous material distant from said portion wherein each of said second sbp members is respectively capable of specifically binding a corresponding first sbp member and said first sbp members are provided in combination with said sample and said portion in said liquid medium.

19. A method for determining the presence of one or more of a plurality of analytes in a sample suspected of containing said analytes, which method comprises
(a) providing in combination (1) a liquid medium containing said sample and a plurality of first sbp members and (2) a portion of bibulous material capable of being traversed by said liquid medium by capillary migration, said bibulous material containing a plurality of second sbp members each non-diffusively bound to a small situs on said bibulous material separated from said portion, the surface area of said situses being substantially less than that of said bibulous material,
each of said second sbp members having the characteristic of binding a corresponding first sbp member
wherein a plurality of third sbp members each capable of binding one of said first sbp members are non-diffusively bound to said bibulous material at least between said small situs and said portion,
(b) allowing said liquid medium to traverse at least a portion of said bibulous material by means of capillary migration, and
(c) detecting the presence or absence of the first sbp members at said situses.

20. The method of claim 19 wherein said bibulous material is in the form of a strip.

21. The method of claim 19 wherein each of said first sbp members is an antibody.

22. The method of claim 19 wherein said second sbp members are each non-diffusively bound to said small situs by virtue of particles non-diffusively bound to said bibulous material at said situs, said particles being conjugated to said second sbp members.

23. The method of claim 19 wherein said first sbp members are each conjugated to a label.

24. The method of claim 23 wherein said first sbp members are detected at said situs by detecting said labels.

25. The method of claim 19 wherein said analytes are drugs and said third sbp members are a drug analogs which are non-diffusively bound to said bibulous material.

26. The method of claim 19 wherein each of said small situses is a band transverse to the direction of traversal of said liquid medium along said bibulous material.

27. A method for determining the presence of one or more of a plurality of analytes in a sample suspected of containing said analyte, which comprises
(a) contacting, with a test solution containing said sample and a plurality of first sbp members, a contact portion of bibulous material capable of being traversed by said test solution by capillary migration,
said bibulous material containing a plurality of second sbp members each non-diffusively bound to a small situs on said bibulous material separate from said contact portion, the surface area of each of said situses being substantially less than that of said bibulous material,
each of said second sbp members having the characteristic of binding a corresponding first sbp member
wherein a plurality of third sbp members each capable of binding one of said first sbp members are non-diffusively bound to said bibulous material at least between said small situs and said portion,
(b) allowing said liquid medium to traverse at least a portion of said bibulous material by means of capillary migration, and
(c) detecting the presence or absence of the first sbp member at said situs.

28. The method of claim 27 wherein said bibulous material is in the form of a strip.

29. The method of claim 27 wherein each of said first sbp members is an antibody.

30. The method of claim 27 wherein said second sbp members are each non-diffusively bound to said small situs by virtue of particles non-diffusively bound to said bibulous material at said situs, said particles being conjugated to said second sbp members.

31. The method of claim 27 wherein said first sbp members are each conjugated to a label.

32. The method of claim 31 wherein said first sbp members are detected at said situs by detecting said labels.

33. The method of claim 27 wherein said analytes are drugs and said third sbp members are drug analogs which are non-diffusively bound to said bibulous material.

34. The method of claim 27 wherein each of said small situses is a band transverse to the direction of traversal of said liquid medium along said bibulous material.

35. A method for determining the presence of one or more of a plurality of analytes in a sample suspected of containing said analytes, which comprises
(a) contacting, with a test solution containing said sample and a plurality of antibodies each corresponding to one of said analytes, and each of said antibodies being conjugated to a label (antibodies—labels), a contact portion of bibulous material capable of being traversed by said test solution by capillary migration,
said bibulous material containing sets of particles, each of said sets being non-diffusively bound to a small situs on said bibulous material separate from said contact portion, the surface area of said situs being substantially less than that of said bibulous material,
said particles having a plurality of sets of members of specific binding pairs ("sbp members") non-diffusively bound thereto, each set of sbp members being respectively capable of binding to one of said antibodies to said analyte when said antibodies are bound to said analyte,
with the proviso that, where said sbp members are able of binding said antibodies to said analyte when said antibodies are not bound to said analyte, a plurality of analogs of said analytes each capable of binding to one of said antibodies to said analyte are non-diffusively bound to said bibulous material between said small situs and said contact portion.
(b) allowing the test solution to traverse at least a portion of said bibulous material by capillary migration, and
(c) detecting the presence or absence of said antibodies-labels at the situs.

36. The method of claim 35 wherein said bibulous material is in the form of a strip.

37. The method of claim 35 wherein each of said antibodies are labelled with an enzyme.

38. The method of claim 35 wherein said small situs is a band traverse to the direction of traversal of said sample along said bibulous material.

39. The method of claim 35 wherein said analytes are drugs and drug analog for each of said drugs is non-diffusively bound to the bibulous material.

40. A method for determining the presence of an analyte in a sample suspected of containing said analyte, which comprises
 (a) contacting, with a test solution containing said sample and a first sbp member, a contact portion of bibulous material capable of being traversed by said test solution by capillary migration,
  said bibulous material containing particles non-diffusively bound to a small situs on said bibulous material separate from said contact portion, the surface area of said situs being substantially less than that of said bibulous material,
  said particles having a member of a specific binding pair ("sbp member") non-diffusively bound thereto, which sbp member is capable of binding to said antibodies to said analyte when said antibodies are bound to said analyte,
  with the proviso that, where said sbp member is able to bind said antibodies to said analyte when said antibodies are not bound to said analyte, an analog of said analyte capable of binding said antibodies to said analyte is non-diffusively bound to said bibulous material between said small situs and said contact portion,
 (b) allowing said test solution to traverse at least a portion of said bibulous material by capillary migration, and
 (c) detecting the presence or absence of said antibodies at said situs.

41. The method of claim 40 wherein said bibulous material is in the form of a strip.

42. The method of claim 40 wherein said antibodies to said analyte are antibodies for human chlorionic gonadotropin.

43. The method of claim 40 wherein said sbp member is antibody for human chorionic gonadotropin.

44. The method of claim 40 wherein said antibodies are labelled with an enzyme.

45. The method of claim 44 wherein a second enzyme is bound to said bibulous material, the enzyme being related in that the product of one enzyme is the substrate of the other.

46. The method of claim 40 for determining a plurality of analytes in said sample, wherein a mixture of specific antibodies to each analyte is combined with the sample and a plurality of corresponding sbp members are each non-diffusively bound to a small situs on said bibulous material wherein each of said sbp members is capable of binding at lease one of the complexes formed between a specific antibody and an analyte.

47. The method of claim 46 wherein an analyte analog for each of said analytes is bound to said bibulous material.

48. The method of claim 40 wherein small situs is a band transverse to the direction of traversal of said sample along said bibulous material.

49. A method of claim 40 wherein said analyte is a drug and a drug analog is non-diffusively bound to the bibulous material.

50. A method for determining the presence of an analyte in sample suspected of containing said analyte, which analyte is a member of a specific binding pair ("sbp member") consisting of ligand and its complementary receptor, which method comprises
 (a) providing in combination (1) a liquid medium containing said sample and a first sbp member capable of binding to said analyte, and (2) a portion of bibulous material capable of being traversed by said liquid medium by capillary migration,
  said bibulous material containing a second sbp member non-diffusively bound to a small situs on said bibulous material separated from said portion, the surface area of said situs being substantially less than that of said bibulous material,
  said second sbp member having the characteristic of binding said first sbp member when said first sbp member is bound to said analyte,
  with the proviso that, where said second sbp member is able to bind said first sbp member when said first sbp member is not bound to said analyte, an analyte analog capable of binding said first sbp member is non-diffusively bound to said bibulous material at least between said small situs and said portion,
 (b) allowing said liquid medium to traverse at least a portion of said bibulous material by means of capillary migration, and
 (c) detecting the presence or absence of the first sbp member at said situs.

51. The method of claim 50 wherein said bibulous material is in the form of a strip.

52. The method of claim 50 wherein said first sbp member is an antibody.

53. The method of claim 50 wherein particles are non-diffusively bound to said bibulous material at said situs, said particles being conjugated to said second sbp member.

54. The method of claim 50 wherein said first sbp member is conjugated to a label.

55. The method of claim 50 wherein said first sbp member is detected at said situs by detecting said label.

56. The method of claim 50 wherein the analyte is a drug and the analyte analog is a drug analog which is non-diffusively bound to said bibulous material.

57. The method of claim 50 wherein the small situs is a band transverse to the direction of traversal of said liquid medium along said bibulous material.

58. The method of claim 50 for determining the presence of a plurality of analytes in said sample, wherein a plurality of corresponding second sbp members are each non-diffusively bound to a small situs on said bibulous material distant from said portion wherein each of said second sbp members is respectively capable of specifically binding a corresponding first sbp member and said first sbp members are provided in combination with said sample and said portion in said liquid medium.

59. A method for determining the presence of an analyte, which comprises
 (a) providing in combination (1) a liquid medium containing said analyte and antibodies to said analyte, said antibodies being conjugated to a label, and (2) a portion of a strip of bibulous material capable of being traversed by said liquid medium by capillary migration,
  said bibulous material containing particles non-diffusively bound to a small situs on said bibulous material separate from said portion,
  the surface area of said situs being substantially less than that of said bibulous material,
  said particles having a member of a specific binding pair ("sbp member") non-diffusively bound thereto, which sbp member is capable of binding to said antibodies to said analyte when said antibodies are bound to said analyte,
  with the proviso that, where said sbp member is able to bind said antibodies to said analyte when said antibodies are not bound to said analyte, an analog of said analyte capable of binding said antibodies to said analyte is non-diffusively bound to said bibulous material between said small situs and said portion, (b) allowing the liquid medium to traverse at least a portion of said bibulous material by capillary migration, and (c) detecting the presence or absence of said first sbp member at the situs.

60. The method of claim 59 wherein said bibulous material is in the form of a strip.

61. The method of claim 59 wherein said antibodies to said analyte are antibodies for human chorionic gonadotropin.

62. The method of claim 59 wherein said sbp member is antibody for human chorionic gonadotropin.

63. The method of claim 59 wherein said antibodies are labelled with an enzyme.

64. The method of claim 63 wherein a second enzyme is bound to said bibulous material, the enzymes being related in that the product of one enzyme is the substrate of the other.

65. The method of claim 59 for determining a plurality of analytes in said sample, wherein a mixture of specific antibodies to each analyte is provided in combination with the sample and the portion of this bibulous material and a plurality of corresponding sbp members are each non-diffusively bound to a small situs on said bibulous material wherein each of said sbp members is capable of binding at least one of the complexes formed between a specific antibody and an analyte.

66. The method of claim 65 wherein an analyte analog for each of said analytes is bound to said bibulous material.

67. The method of claim 59 wherein said small situs is a band traverse to the direction of traversal of said liquid medium along said bibulous material.

68. The method of claim 59 wherein said analyte is a drug and a drug analog is non-diffusively bound to the bibulous material.

69. A method for determining the presence of an analyte, which method comprises (a) providing in combination (1) a liquid medium containing said analyte and a first sbp member capable of binding to said analyte, and (2) a portion of bibulous material capable of being traversed by said liquid medium by capillary migration, said bibulous material containing a second sbp member non-diffusively bound to a small situs on said bibulous material separated from said portion, the surface area of said situs being substantially less than that of said bibulous material, said second sbp member having the characteristic of binding said first sbp member when said first sbp member is bound to said analyte, with the proviso that, where said second sbp member is able to bind said first sbp member when said first sbp member is not bound to said analyte, an analyte analog capable of binding said first sbp member is non-diffusively bound to said bibulous material at least between said small situs and said portion, (b) allowing said liquid medium to traverse at least a portion of said bibulous material by means of capillary migration, and (c) detecting the presence or absence of the first sbp member at said situs.

70. The method of claim 69 wherein said bibulous material is in the form of a strip.

71. The method of claim 69 wherein said first sbp member is an antibody.

72. The method of claim 69 wherein particles are non-diffusively bound to said bibulous material at said situs, said particles being conjugated to said second sbp member.

73. The method of claim 69 wherein said first sbp member is conjugated to a label.

74. The method of claim 73 wherein said first sbp member is detected at said situs by detecting said label.

75. The method of claim 69 wherein the analyte is a drug and the analyte analog is a drug analog which is non-diffusively bound to said bibulous material.

76. The method of claim 69 wherein the small situs is a band transverse to the direction of traversal of said liquid medium along said bibulous material.

77. The method of claim 69 for determining the presence of a plurality of analytes in said sample, wherein a plurality of corresponding second sbp members are each non-diffusively bound to a small situs on said bibulous material distant from said portion wherein each of said second sbp members is respectively capable of specifically binding a corresponding first sbp member and said first sbp members are provided in combination with said sample and said portion in said liquid medium.

78. A device for determining the presence of an analyte, which device comprises a bibulous material, the pores of at least a portion of which have particles infiltrated in the form of a pattern therein, said particles having a member of a specific binding pair non-diffusively bound thereto.

79. The device of claim 78 wherein said sbp member is an antibody.

80. The device of claim 78 wherein said sbp member is a ligand.

81. The device of claim 78 wherein said pattern is a dot.

82. The device of claim 78 wherein said pattern is a line.

83. The device of claim 78 wherein said pattern is a curve.

84. The device of claim 78 wherein said pattern is an abbreviated name of an analyte.

85. The device of claim 78 wherein said pattern is a plus sign.

86. The device of claim 78 wherein said particles are non-diffusively bound within said pores.

87. The device of claim 78 wherein said particles are latex particles.

88. The device of claim 78 which further comprises a support for said bibulous material.

89. The device of claim 78 wherein a plurality of patterns are formed on said bibulous material.

90. The device of claim 78 wherein said patterns are the same.

91. The device of claim 78 wherein each of said patterns are different.

92. A device for determining the presence of an analyte in a test solution comprised of a first member of a specific binding pair and a sample of containing the analyte, which comprises bibulous material capable of traversal by said test solution by capillary migration, said bibulous material having a first portion for contacting said test solution ("contact portion") and a second sbp member non-diffusively bound to a second portion of said bibulous material, separated from said contact portion, the surface area of said second portion being substantially less than that of said bibulous material, said second sbp member having the characteristic of binding said first sbp member, and a third sbp member, capable of binding said first sbp member, non-diffusively bound to said bibulous material at least between said second portion and said contact portion.

93. The device of claim 92 wherein said bibulous material is a paper strip.

94. The device of claim 92 wherein said first sbp member is an antibody.

95. The device of claim 92 wherein particles are non-diffusively bound to said portion, said particles being conjugated to said second sbp member.

96. The device of claim 92 wherein said third sbp member is an analyte analog.

97. The device of claim 92 wherein the analyte is a drug.

98. The device of claim 93 wherein the portion is a band transverse to the direction of traversal of said test solution along said strip.

99. The device of claim 92 wherein the signal produced at said portion has a sharp-edged distinctive pattern.

100. The device of claim 92 wherein said first sbp member is conjugated to an enzyme and a second enzyme is bound to said bibulous material, the enzymes being related in that the product of one enzyme is the substrate for the others.

101. The device of claim 92 for determining the presence of a plurality of analytes in said test solution wherein each of a set of first sbp members is respectively non-diffusively bound to a different small portion on said strip separate from said contact portion wherein each set of sbp members is capable of binding to a specific complex of an analyte and a second sbp member.

102. A device for determining the presence of an analyte in a test solution comprised of a first specific binding pair (sbp) member and a sample suspected of containing said analyte, which comprises a strip of bibulous material capable of being traversed by said test solution by capillary migration, said strip having an end portion for contacting said test solution and a second sbp member non-diffusively bound to said strip at a small situs separated from said end portion, said situs having a surface area substantially less than that of said strip, through which situs said test solution passes as it traverses said strip, and a third sbp member, capable of binding said first sbp member, non-diffusively bound to said strip at least between said small situs and said end portion.

103. The device of claim 102 wherein said strip of bibulous material is a paper strip.

104. The device of claim 102 wherein said first sbp member is an antibody.

105. The device of claim 102 wherein particles are non-diffusively bound to said strip at said situs, said particles being conjugated to said second sbp member.

106. The device of claim 102, wherein said third sbp member is an analyte analog.

107. The device of claim 102 wherein the analyte is a drug.

108. The device of claim 102 wherein the small situs is a band transverse to the direction of traversal of said test solution along said strip.

109. The device of claim 102 wherein the signal produced at the small situs has a sharp-edged distinctive pattern.

110. The device of claim 102 wherein said first sbp member is conjugated to an enzyme and a second enzyme is bound to said strip, the enzymes being related in that the product of one enzyme is the substrate for the other.

111. The device of claim 102 for determining the presence of a plurality of analytes in said test solution wherein each of a set of first sbp members is respectively non-diffusively bound to a different small situs on said strip separate from said end portion wherein each set of sbp member is capable of binding to a specific complex of an analyte and a second sbp member.

112. A kit for determining the presence of an analyte in a test solution, comprising in a packaged combination (a) the device of claim 92, (b) other members of a signal producing system for producing a detectible signal in the presence of said analyte as required, and (c) ancillary materials as required.

113. A multizone test device for the specific binding assay determination of an analyte in a liquid test medium involving binding among (i) the analyte, (ii) a labeled or immobilized form of the analyte or of a binding analog thereof, and (iii) an immobilized or labeled form, respectively, of a binding partner of the analyte; the labeled one of the analyte, analog thereof, or binding partner being a labeled reagent comprising a detectable chemical group having a detectable physical property, the test device comprising, in fluid flow contact, (1) a reagent zone comprising a solid, porous matrix incorporated with an immobilized one of the analyte, analog thereof, or binding partner, and (2) a detection zone comprising a solid, porous matrix for receiving and measuring labeled reagent which migrates into said detection zone and incorporated with an immobilized form of a binding substance for the labeled reagent.

114. The test device of claim 113 wherein the labeled reagent comprises an antibody, or a fragment thereof having an intact binding site for protein A, and the binding substance for the labeled reagent immobilized in the detection zone.

115. The test device of claim 113 wherein the labeled reagent is incorporated in said reagent zone and comprises a detectable chemical group, is a fluorescer or a chromophore.

116. The test device of claim 113 wherein the binding substance for the labeled reagent is immobilized in the detection zone by being covalently couples to the matrix comprised therein.

117. The test device of claim 113 wherein the binding substance for the labeled reagent is immobilized in the detection zone by being attached to a high molecular weight polymeric substance dispersed in said matrix.

118. The test device of claim 113 wherein the binding partner for the analyte is an antibody or a fragment thereof.

119. The test device of claim 113 which comprises a solid, porous chromatographic element and wherein the reagent and detection zones are discrete sections of such element.

120. The test device of claim 113 wherein the immobilized binding substance for the labeled reagent in the detection zone is an antibody, or a fragment thereof, which binds the labeled reagent.

121. The test device of claim 120 wherein the labeled reagent comprises an antibody, or a fragment thereof, to the analyte and the binding substance for the labeled reagent immobilized in the detection zone is an antibody, or a fragment thereof, to said anti-analyte antibody or fragment thereof.

122. The test device of claim 113 wherein the immobilized binding substance for the labeled reagent in the detection zone is an adsorbent material for the labeled reagent.

123. The test device of claim 122 wherein the absorbent material is an ion exchange material.

124. The test device of claim 113 wherein the labeled reagent is incorporated in said reagent zone and additionally comprises a ligand moiety and the immobilized binding substance for the labeled reagent in the detection zone is a binding partner of such ligand moiety.

125. The test device of claim 124 wherein the ligand moiety is a carbohydrate or a lectin which specifically binds therewith, and the binding partner for the ligand moiety is the other thereof.

126. The test device of claim 124 wherein the binding partner of the ligand moiety is a protein which specifically recognizes such moiety.

127. The test device of claim 126 wherein the ligand moiety is biotin or avidin, and the binding partner for the ligand moiety is the other thereof.

128. The test device of claim 126 wherein the protein which specifically recognizes the ligand moiety is an antibody or a fragment thereof.

129. The test device of claim 128 wherein the ligand moiety is a hapten.

* * * * *

UNITED STATES PATENT AND TRADEMARK OFFICE
CERTIFICATE OF CORRECTION

PATENT NO. : 5,716,778
DATED : February 10, 1998
INVENTOR(S) : Weng et al.

It is certified that error appears in the above-identified patent and that said Letters Patent is hereby corrected as shown below:

Column 23, line 61, change "in sample" to --in a sample--.

Column 26, line 55, change "pair and" to --pair (sbp member) and--.

Signed and Sealed this

Ninth Day of June, 1998

Attest:

BRUCE LEHMAN

*Attesting Officer*  *Commissioner of Patents and Trademarks*